United States Patent [19]

Golding

[11] Patent Number: 4,628,742

[45] Date of Patent: Dec. 16, 1986

[54] TENSILE STRENGTH TESTER FOR HAIR

[75] Inventor: Frank E. Golding, Hacienda Heights, Calif.

[73] Assignee: Redken Laboratories, Canoga Park, Calif.

[21] Appl. No.: 735,688

[22] Filed: May 20, 1985

[51] Int. Cl.[4] .............................................. G01N 3/08
[52] U.S. Cl. ........................................ 73/829; 73/831
[58] Field of Search ................. 73/829, 831, 828, 856

[56] References Cited

U.S. PATENT DOCUMENTS 3,881,346  5/1975  Scheucher ............................ 73/829
4,286,469  9/1981  Trias ..................................... 73/829

Primary Examiner—Anthony V. Ciarlante
Attorney, Agent, or Firm—Christie,Parker&Hale

[57] ABSTRACT

Apparatus for measuring tensile strength of hair samples in which the test is controlled automatically to provide the average value of a plurality of hair samples. The apparatus is digitally controlled to provide a rapid testing cycle time. Tension is applied by a pivoted arm, and rotated by a solenoid that is controlled digitally to provide substantially constant velocity to the arm. A strain gage secured to the arm measures the force extended by the arm in tensioning the hair sample.

13 Claims, 7 Drawing Figures

4,628,742

TENSILE STRENGTH TESTER FOR HAIR

FIELD OF THE INVENTION

This invention relates to apparatus for measuring the tensile strength of human hair.

BACKGROUND OF THE INVENTION

In the scientific care and treatment of hair, one of the properties which has been found significant in analyzing the condition of the hair is the tensile strength of the hair. Apparatus for measuring the tensile properties of human hair are described in U.S. Pat. Nos. 3,921,443 and 4,061,022, both assigned to the same assignee as the present invention. These patents describe testing devices in which a strand of hair is clamped between two relatively moving posts. One post is driven at a constant velocity by a spring or motor, and the movement of the second post against the resistance of a calibrated spring is used to measure the tensile strength of the hair. These devices, while providing effective measurement of hair tension, are somewhat awkward to use, hair samples are not easily mounted, the measurement cycle times are relatively slow, and the requirement that both posts must move results in a complex and costly mechanical device.

SUMMARY OF THE INVENTION

The present invention is directed to an improved design for a hair testing apparatus of the type described in the above identified patents. The present invention is characterized by its simplicity of design, its improved hair sample clamping arrangement, its reduced sampling time, and its ability to measure and average the results from a number of hair samples.

This is accomplished by providing an arrangement in which the hair clamping means is fixedly secured to the frame and simultaneously clamps both ends of a strand of hair to form a loop. A single pivoted arm engages the bight portion of the hair loop. A solenoid drive moves the arm against the loop to put the hair under increasing tension and to stretch the hair strand until it breaks. A strain gage mounted on the arm senses the force exerted by the arm against the hair strand. A linear potentiometer senses the changing position of the arm. A microprocessor records and correlates in digital form the force and position information from the strain gage and potentiometer, and releases the arm when the hair strand is broken, allowing another sample to be immediately loaded into the clamping means for another test. The microprocessor allows a number of successive samples to be averaged, the accumulated average being displayed digitally to the operator.

DESCRIPTION OF THE DRAWINGS

For a better understanding of the invention reference should be made to the accompanying drawings, wherein.

DETAILED DESCRIPTION

Figure 1:
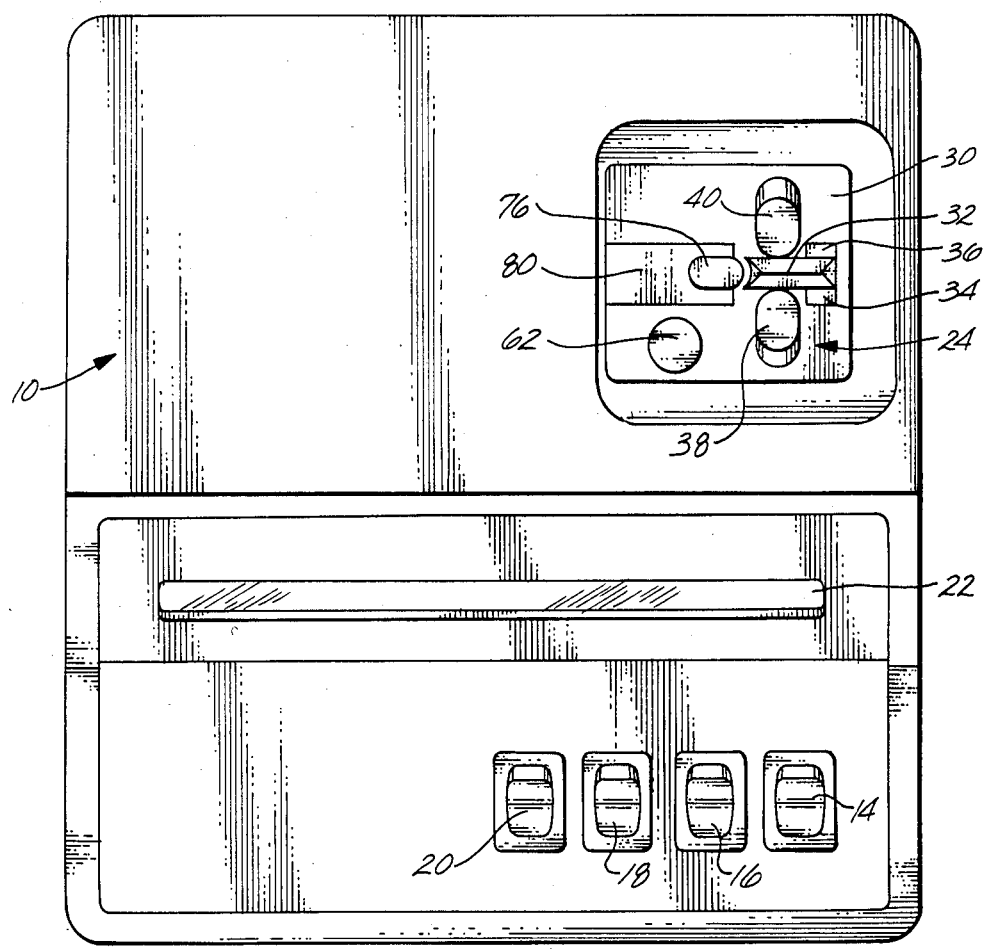
FIG. 1 is a top view of the testing apparatus of the present invention.
Figure 2:
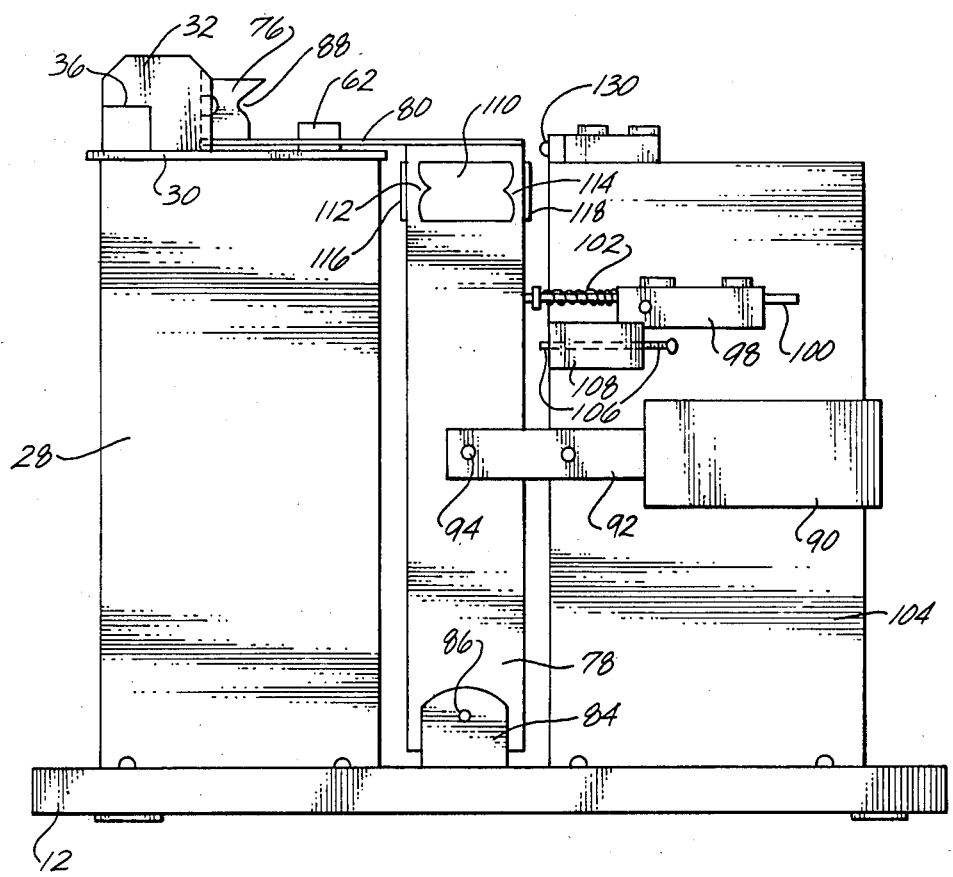
FIG. 2 is a side view of the apparatus with the cover removed.

Referring to FIGS. 1 and 2 in detail, the numeral 10 indicates generally a cover for housing the testing apparatus which is mounted on top of a frame base 12. The cover includes four control switches, and On/Off switch 14, a Clear switch 16, a Delete switch 18 and a Start Test switch 20. Read-out of test results is indicated on a liquid crystal display screen 22. A hair clamping assembly, indicated generally at 24, is supported in an opening in the cover from the base 12 by support brackets 26 and 28 anchored to the frame base.

Figure 3:
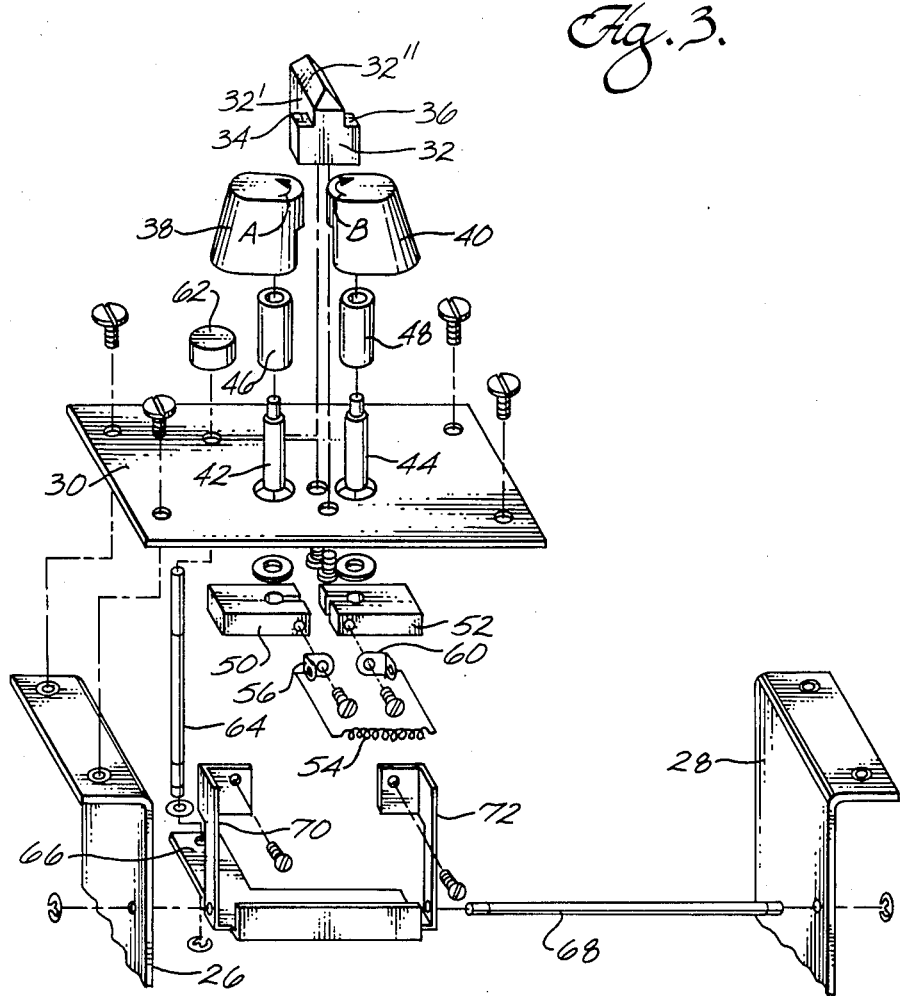
FIG. 3 is an exploded view of the hair clamping assembly.
Figure 4:
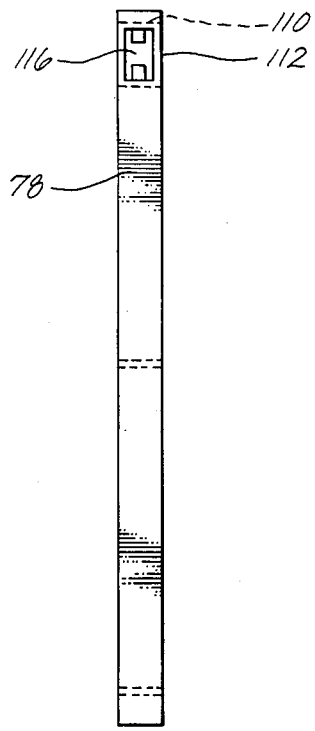
FIG. 4 is a detail view of the tensioning arm.

The hair clamping assembly is shown in more detail in the exploded view of FIG. 3. The support brackets 26 and 28 support a rigid plate 30 to which is bolted or otherwise secured a projecting post 32. The post is designed with a central portion 32' having an inverted V-shaped or beveled top surface 32''. A pair of shoulders 34 and 36, are formed on either side of the post by a widened end section of the post. The shoulders 34 and 36 act as a stop for positioning a strand of hair formed in a U-shaped loop. The ends of the loop are clamped on the sides of the post 32 against the shoulders 34 and 36 by a pair of rotating clamping members 38 and 40. The clamping members 38 and 40 are secured to the ends of a pair of shafts 42 and 44. The shafts are journaled in bearing sleeves 46 and 48 that are rigidly attached to the plate 30. The upper ends of the shafts 42 and 44 are connected to the clamping members 38 and 40 while the lower ends are attached respectively to a pair of control arms 50 and 52. A tension spring 54 is secured at each end to brackets 56 and 60 that are secured to the sides of the control arms 50 and 52. The spring 54 acts to rotate the arms 50 and 52 and clamping members 38 and 40 in the direction indicated by the arrows A and B. The inner surfaces of the clamping members are eccentric in relation to the axis of rotation of the shafts 42 and 44, so that as the clamping members are rotated by the spring 54, the inner surfaces of the clamping members move into wedging engagement with the sides of the post 32. For wedging to occur, the frictional force between the hair and clamping surface must be greater than the pulling force exerted on the hair sample. If l is the eccentric offset between the axis of rotation of the clamping member and the center of curvature of the surface engaging the hair, it can be shown that $l < C L$ where C is the coefficient of friction between the hair and clamping surface and L is the distance between the axis of rotation and the point of contact. Rotation of the clamping members 38 and 40 in the opposite direction against the tension of the spring 54 causes their inner surfaces to move away from the post to form gaps into which the two ends of the hair loop can be easily inserted over the beveled top of the port 32.

To simplify the sample loading operation, both clamping members 38 and 40 can be rotated simultaneously out of engagement with the post 32 by pressing down on a push button 62. The push button is connected by a rod 64 to a control lever 66 that is hingedly supported between the brackets 26 and 28 by a hinge pin 68. The control lever 66 includes a pair of arms 70 and 72, the upper ends of which press against and rotate the arms 50 and 52 when the push button 62 is depressed. Thus the arms 50 and 52 are simultaneously rotated against the tension of the spring 54 to move the clamping members 38 and 40 out of contact with the post 32. After the ends of a hair sample are inserted in the gaps between the clamping members 38 and 40 and the post 32, release of the push button 62 allows the spring 54 to rotate the clamping members 38 and 40 into hair clamping engagement with the post 32. This arrangement also allows either one of the clamping members 38 or 40 to be independently rotated by hand against the action of the spring 54, thus permitting either end of the hair loop to be clamped or released as required.

Positioned adjacent the fixed post 32 is a moving post 76 which is secured to the upper end of a pivoted tensioning arm 78. Because the upper end of the pivoted arm 78 is offset from the moving post 76, a post mounting bracket 80 is provided which supports the moving post 76 immediately adjacent the fixed post 32 in the initial operating condition. The lower end of the tensioning arm is pivotally supported from the frame base 12 by a bracket 84 and hinge pin 86. As best seen in FIG. 2, the moving post 76 is notched at 88, the notch being positioned in the same horizontal plane as the shoulders 34 and 36. When loading the strand of hair being tested, it is looped around the notch 88, with the ends of the hair strand held against the shoulders 34 and 36 where they are clamped against the post 32 by the clamping members 38 and 40, in the manner described above.

The tensioning arm 78 is linked to a solenoid 90, the armature 92 of which is pivotally connected to the arm 78 by a pin 94, as viewed in FIG. 2. Energizing the coil of the solenoid 90 causes the armature 92 and associated arm 78 to move to the right, stretching the hair loop sample between the fixed post 32 and the moving post 76. Movement of the tensioning arm 78 is sensed by a linear potentiometer 98 that is actuated by a pin 100 which normally is lightly pressed against the arm 78 by a compression spring 102. The solenoid 90 and potentiometer 98 are rigidly mounted to the frame base 12 by a mounting bracket 104. An adjustable stop in the form of a screw 106 threaded in a block 108 engages the tensioning arm 78 to limit the maximum travel of the moving post 76 away from the post 32.

The upper end of the tensioning arm 78 has an opening 110 extending through the arm. The opening 110 forms two relatively thin connecting sections 112 and 114. A pair of bonded strain gages 116 and 118 are cemented to the edges of the tensioning arm 78 adjacent the thin sections 112 and 114 for sensing any slight deformation or deflection of the thin sections exerted by the strand of hair against the moving post 76.

Figure 5:
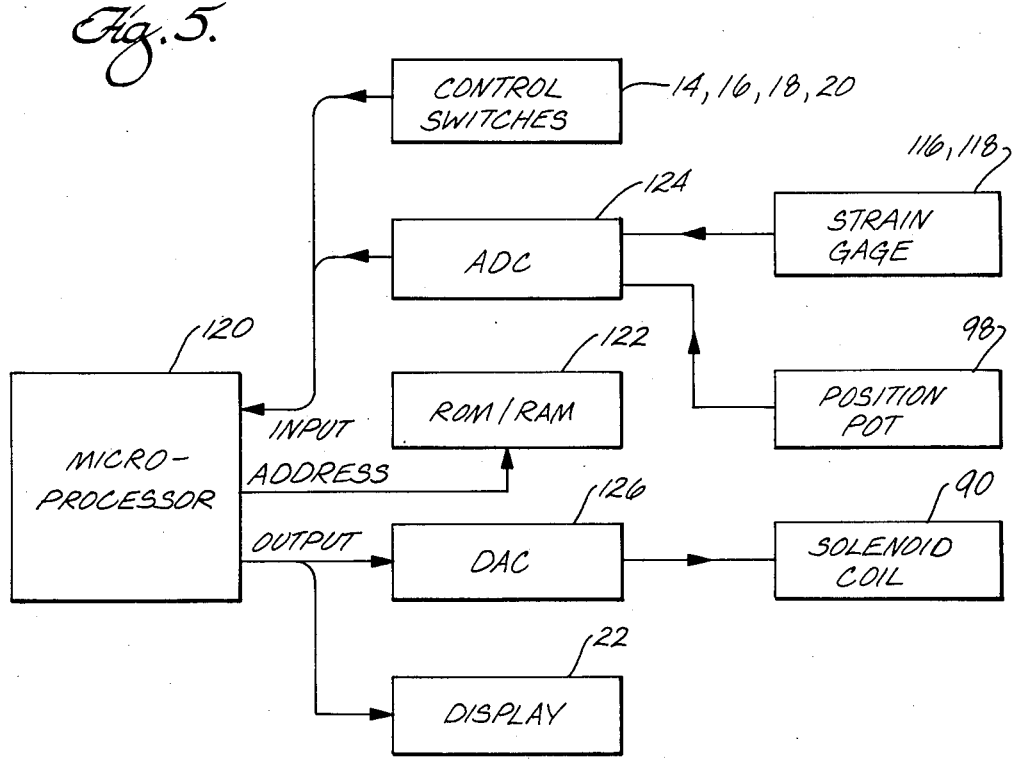
FIG. 5 is a schematic block diagram of the control circuit.

Control of the testing apparatus is by a digital control circuit shown in FIG. 5. The control circuit includes a microprocessor 120 controlled by a program stored in an addressable ROM/RAM memory 122, which is addressable by the microprocessor. Input voltages from the strain gages 116 and 118, and the position potentiometer 98 are digitized by an analogue-to-digital converter 124 for input to the microprocessor. Output information from the microprocessor is used to control the solenoid 90 through a digital-to-analogue converter 126. Output information from the processor is also applied to the digital display 22.

Figure 6:
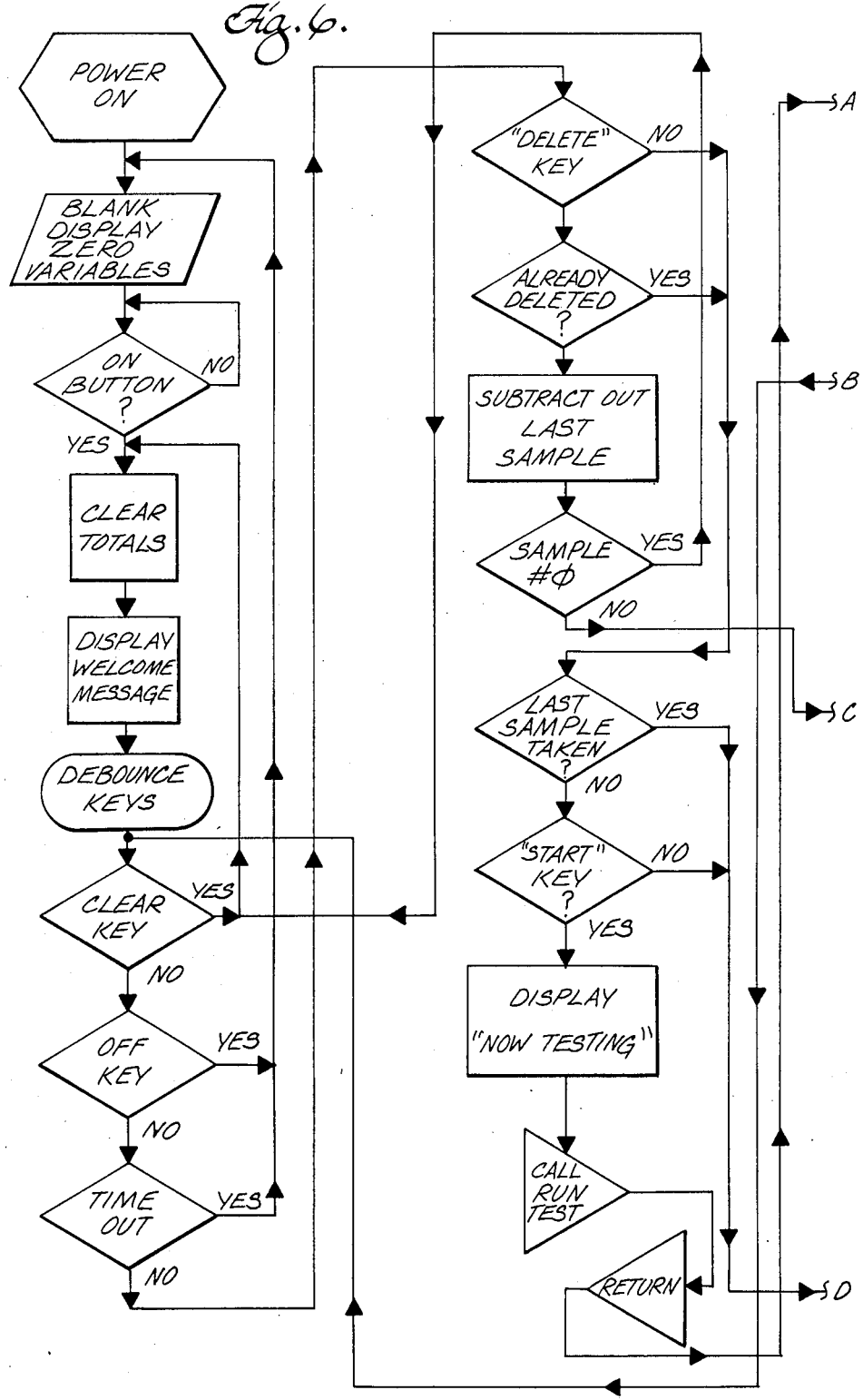
FIGS. 6-6A are a flow diagram of the control program for the microprocessor.
Figure 6A:
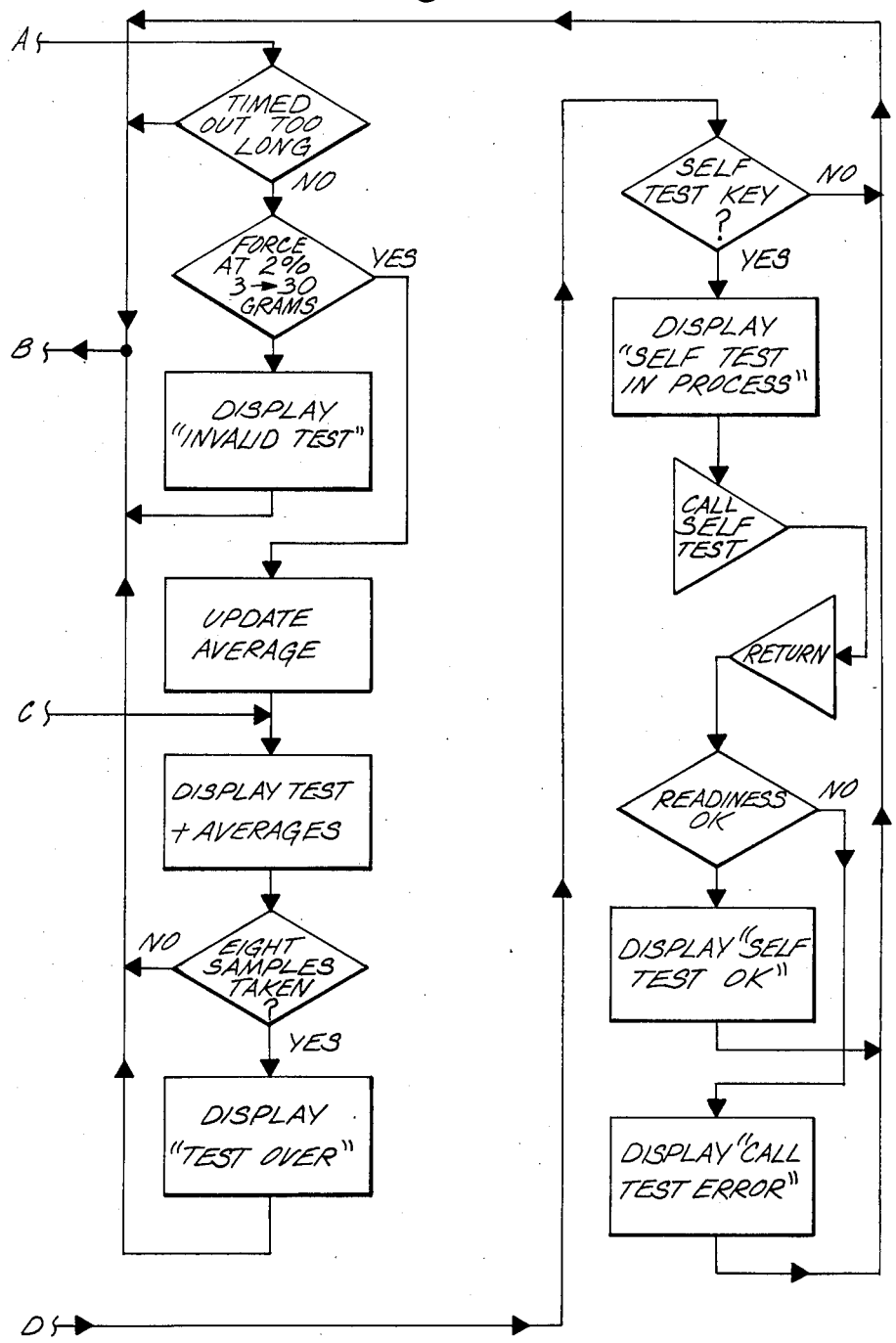

Operation of the microprocessor 120 is under control of a program stored in the ROM, the basic steps of the program being shown by the flow diagram of FIG. 6. After the power is turned on to the system, the processor is initialized by setting the variables to zero and clearing the display. The processor then waits for the On-switch 14 to be activated. When the button is activated to start a measurement, a "welcome" message is displayed on the screen. The program then tests to determine whether the Clear key has been activated. If not, it checks to see whether the Off-key has been activated, and if not, it checks to see whether there has been a three-minute timeout. Finally, if none of these conditions have occurred, it checks to see if the Delete key has been activated. If not, the test continues to determine if a sample has been taken, and if not, to determine whether the Start key has been activated. Assuming the last sample has not been taken and the Start key has been activated, a test of the sample is initiated by calling a "Run Test" routine and indicating on the display that the apparatus is "Now Testing".

During the test run, the microprocessor generates a series of increasing digital values which are converted to an increasing voltage by the digital-to-analogue converter. Thus the power to the solenoid is continuously increased, causing the hair sample to be stretched more and more until it breaks. As the hair sample is stretched, the microcomputer is recording the digitized output of the strain gages and potentiometer. If the output of the strain gages goes to zero, indicating the hair sample has broken, the microprocessor reduces the output to the solenoid to zero and terminates the "Test Run" routine.

When the test run is complete, a check is made to determine that the test was completed within a maximum allowable time. If the test did not take too long, the data is checked to determine the force required to produce a 1% elongation. If the force was under three grams or over 30 grams with a 1% elongation indicated by the potentiometer output, this signals that either the sample hair slipped in the clamp and therefore was not under sufficient tension, the hair loop was loose around the moving post, or the hair was stretched too tight around the moving post before the test commenced. If any of these conditions pertain, an appropriate message is displayed and the program loops back to the beginning.

If the force at 1% elongation was within prescribed limits, the recorded test data is used to update the sample average from previous samples. The program is designed to repeat the test on eight hair samples, generating an average value for the force required to produce a 10% elongation of each of the hair samples and also an average of the yield force resulting in breakage of each of the hair samples. Both the results of the sample test and the averages are then displayed on the display screen. If eight samples have been taken, the display indicates that the test is completed and the program loops back to the beginning. However, if less than eight samples have been taken, the program loops back to the beginning without affecting the display and the test is repeated on the next sample. Any test sample can be deleted from the average by operating the Delete switch 18 if the operator has reason to believe the test was not valid.

One feature of the invention is a self-calibration test, indicated by the program flow chart of FIG. 6. After the last sample is taken or if the Start key is not actuated and a Self-Test key is actuated, a self-test routine is called in which the solenoid 90 is fully energized moving the tensioning arm 78 over against the calibration stop 106. This brings the arm into contact with a spring-loaded calibration button 130 which exerts a predetermined load against the outer end of the tensioning arm 78 when the arm is against the stop. If the resulting digitized output of the strain gages is within predetermined calibration limits, the display indicates that the self-test is okay and the program loops back to the beginning. However, if the digitized output from the strain gages is not within the test limits, the display indicates that there is a calibration test error, in which event the operator should have the unit serviced and recalibrated before continuing with any hair sample test. The calibration of the linear potentiometer 98 is also verified by comparing the output of the potentiometer to a predetermined reference voltage when the arm is moved against the set screw 106.

From the above description it will be seen that an improved hair tester has been provided which allows a simple one-step operation for inserting a hair sample. Because the hair clamping arrangement simultaneously clamps both ends of the hair to form a loop and is anchored directly to the frame and not to any moving assembly, insertion of the hair sample is made easy. The single pivoted arm for tensioning the hair sample and measuring the tension force achieves a greatly simplified and rugged construction. Because of the digitally controlled sampling cycle, the sampling time can be reduced to a minimum. By averaging a number of hair samples from a person, a more meaningful evaluation is achieved.

What is claimed is:

1. Apparatus for testing hair quality comprising:
a frame, clamping means fixedly secured to the frame for holding the ends of a hair strand together to form a loop, a movable member engaging the loop, solenoid drive means for applying a force to the movable member away from the clamping means to stretch and elongate the loop, control means for increasing the force exerted by the solenoid at a controlled rate, means for measuring the force exerted by the moving member against the loop, means for measuring the change in position of the movable member relative to the frame, and means responsive to the force measuring means for deenergizing the solenoid means to return the movable member to its initial position relative to the clamping means in response to a decrease in the measured force.

2. Apparatus of claim 1 wherein the clamping means includes a post secured to the frame, a pair of rotating clamping arms on opposite sides of the post, each arm being rotatable into and out of engagement with the post about an axis parallel to the post, and spring means urging the rotation of the arms into engagement with the post, the ends of the hair being clamped against opposite sides of the post by the rotation of the respective arms.

3. Apparatus of claim 1 wherein the movable member includes an arm pivoted at one end to the frame and extending adjacent the clamping means at the outer end, the loop of hair held by the clamping means extending around the outer end of the arm, said drive means being mounted on the frame and secured to the arm for rotating the arm away from the clamping means when said drive means is energized, and spring means normally urging the arm back toward the clamping means for returning the arm to its initial position when the drive means is deenergized.

4. Apparatus of claim 3 wherein the means for measuring the force exerted by the moving member includes strain gage means secured to the arm between the outer end of the arm and the drive means for sensing bending of the arm by the restraining force of the hair loop.

5. Apparatus of claim 4 wherein the means for measuring the change in position of the movable arm includes a potentiometer actuated by the arm.

6. Apparatus of claim 5 further comprising calibration means including spring-loaded stop means engaged by the outer end of the arm with rotation of the arm by the solenoid drive means, the spring-loaded stop means producing a predetermined force on the outer end of the arm and the strain gage when fully engaged by the arm.

7. The apparatus of claim 4 further including means storing the output of the strain gage and the output of the position measuring means, means displaying the stored output value of the strain gage for a predetermined change in position of the moving arm, means for averaging said displayed output values for a plurality of hair samples, and means for displaying the output of the averaging means.

8. Apparatus of claim 7 further including means for displaying the stored output of the position measuring means corresponding to the drop in the strain gage output when the hair sample breaks.

9. Apparatus of claim 8 further including means for averaging the stored outputs of the position measuring means for a plurality of hair samples, and means displaying the average of said stored outputs.

10. A hair testing device comprising:
a frame, a fixed post secured to and extending vertically from the frame, a pair of rotating eccentric clamping arms engaging the post on opposite sides thereof, means for simultaneously rotating the clamping members in and out of engagement with the post, the clamping arms clamping the ends of a hair strand against the post to secure the strand in a closed loop, a movable post engaging the loop of hair, means driving the moving post away from the fixed post to stretch the hair strand between the fixed and moving posts, and means for measuring the force extended on the posts by the hair strand as it is stretched.

11. Apparatus of claim 10 wherein said means for measuring the force exerted on the posts includes a strain gage secured to one of the posts for sensing any deflection of the post produced by the tension of the hair strand as the posts move apart.

12. Apparatus of claim 11 further including means for measuring the position of the moving post.

13. Apparatus of claim 10 further including means for measuring the position of the moving post.

* * * * *